(12) United States Patent
Giesemann et al.

(10) Patent No.: US 12,310,822 B2
(45) Date of Patent: May 27, 2025

(54) MULTI-LAYERED DRESSING

(71) Applicants: Leslie Giesemann, Solana Beach, CA (US); Irene Rodriguez, Hermosa Beach, CA (US)

(72) Inventors: Leslie Giesemann, Solana Beach, CA (US); Irene Rodriguez, Hermosa Beach, CA (US)

(*) Notice: Subject to any disclaimer, the term of this patent is extended or adjusted under 35 U.S.C. 154(b) by 303 days.

(21) Appl. No.: 17/013,523

(22) Filed: Sep. 4, 2020

(65) Prior Publication Data
US 2021/0069021 A1 Mar. 11, 2021

Related U.S. Application Data

(60) Provisional application No. 62/896,433, filed on Sep. 5, 2019.

(51) Int. Cl.
*A61F 13/00* (2024.01)
*A61F 13/0203* (2024.01)

(52) U.S. Cl.
CPC .... *A61F 13/00063* (2013.01); *A61F 13/0213* (2013.01); *A61F 2013/00182* (2013.01)

(58) Field of Classification Search
CPC .................. A61F 13/0213; A61F 2013/00182
See application file for complete search history.

(56) References Cited

U.S. PATENT DOCUMENTS

| | | | | |
|---|---|---|---|---|
| 5,106,629 A | * | 4/1992 | Cartmell | A61F 13/0203 424/443 |
| 5,372,586 A | * | 12/1994 | Haber | A61M 5/31596 604/91 |
| 6,447,486 B1 | * | 9/2002 | Tollini | A61M 25/02 604/180 |
| 2006/0129080 A1 | * | 6/2006 | Bjornberg | A61F 13/01042 602/56 |
| 2007/0010778 A1 | * | 1/2007 | Burrell | A61M 25/02 602/54 |
| 2007/0293800 A1 | * | 12/2007 | McMaken | A61L 31/16 602/48 |
| 2009/0005722 A1 | * | 1/2009 | Jennings-Spring | A61F 13/00063 604/20 |
| 2010/0305490 A1 | * | 12/2010 | Coulthard | A61F 13/022 604/313 |
| 2010/0331785 A1 | * | 12/2010 | Fabo | A61M 16/047 604/180 |
| 2016/0008576 A1 | * | 1/2016 | Lee | A61M 25/02 604/174 |
| 2016/0354535 A1 | * | 12/2016 | Blott | A61M 1/92 |
| 2019/0008690 A1 | * | 1/2019 | Adie | A61M 1/84 |

* cited by examiner

*Primary Examiner* — Rebecca E Eisenberg
*Assistant Examiner* — Kate Elizabeth Strachan
(74) *Attorney, Agent, or Firm* — Jaquez Land Greenhaus & McFarland, LLP; Bruce W. Greenhaus (57) ABSTRACT

A dressing for use with percutaneous tubes/drains/pins and tracheostomies that is designed to be impermeable to aid in the prevention of leakage of body secretions or fluids and to help prevent microbes from entering the body around the percutaneous device from the outside of the dressing. The dressing includes three layers or more including a layer having antimicrobial, bacteriocidal, or hemostatic agents, a cushioned absorbent layer covered by an outer see through impermeable adhesive layer.

25 Claims, 5 Drawing Sheets

MULTI-LAYERED DRESSING

CROSS REFERENCE TO RELATED APPLICATIONS

The present application claims priority to U.S. Provisional Application No. 62/896,433 filed Sep. 5, 2019, entitled MULTI-LAYERED DRESSING, the entire contents of which is hereby expressly incorporated by reference.

FIELD

The present invention relates generally to the field of surgery, and more specifically, to a single unit multi-layered and/or concentric layered dressing with or without a keyhole opening, with or without phalanges for percutaneous tubing/drains/pins and surgical sites.

BACKGROUND

Percutaneous tubes are used in many medical procedures and may be left in place after the procedure. In some cases, the percutaneous tube may be used as a drain to drain fluids from the body and may be secured to the skin with an adhesive device or suture. In some cases, the percutaneous tube may be a chest tube that can help drain air, blood, or fluid from the space surrounding the lungs, called the pleural space. In some cases, the percutaneous tube may be a tracheostomy tube inserted into the trachea to be used an airway. In some cases, the percutaneous tube may be a percutaneous pin used for the stabilization of unstable bones or fractures. In some cases, the percutaneous tube may be a percutaneous endoscopic gastronomy (PEG) tube used to deliver food directly into the stomach. In some cases, the percutaneous tube may be a percutaneous cholecystostomy tube used to drain gallbladder fluid.

There is commonly a discharge of blood and/or fluid around the percutaneous tube where it exits the body. This discharge may include the fluids being removed through the tube as well as blood and other medical fluids which are present in the body. The area around the percutaneous tube should be cleaned and/or medicated prior to covering with a sterile dressing.

The dressings around the percutaneous tube sites and surgical sites are currently individual layers of square material applied and attached to the area with adhesive tape strips. This process is awkward and time consuming because the dressings are applied manually layer by layer with each layer on top of the layer below it. This makes the dressings bulky, awkward, and inefficient in performing the actions described above.

The area should be monitored to prevent infection and assure proper healing. The dressing materials may not be transparent, so the dressing must be completely removed to view the area.

While in the hospital, the dressings are applied and changed during rounds or by the nursing staff. Outpatients may have to change the dressing themselves, without medical personnel, which can sometimes be difficult for the patient to put the individual layers of dressing on correctly.

Accordingly, there remains a need for a single dressing that provides solutions to the problems of current design. The present invention is directed toward meeting these needs.

SUMMARY

The present invention is directed to a dressing for use with percutaneous tubes/drains/pins, tracheostomies and surgical sites. Its outer layer is designed to be impermeable, thus an aid in the prevention of leakage of body secretions or fluids and to help prevent microbes from entering the body around the percutaneous device from the outside of the dressing. This will allow the patient to shower with the dressing in place. Its outer layer is also transparent which allows the viewer the ability to see the components touching the transparent outer covering. The dressing includes any combination of multiple concentric (denoting shapes which share the same center, the larger of which completely surrounding the smaller, and/or overlapping concentric, or completely overlapping components (layers). Each component of this single dressing will have a function. The components will be combined in any combination of materials needed to perform the function for which it is applied. For example: therapeutic material, such as a bactericidal, a hemostatic, and absorbent material, may be combined in one single dressing. Another dressing could combine medicinal products such as analgesic, CBD, or marijuana derived substance with a cushioned absorbent layer, with all covered by an outer see through impermeable adhesive layer. Thus illustrating how these components can be combined and customized to the medical need of the wearer. Thus making a less bulky and easier to apply and remove dressing for its intended use.

DETAILED DESCRIPTION

Reference will now be made in detail to the present embodiments of the invention, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc., may be used herein to describe various limitations, elements, components, regions, layers, and/or sections, these limitations, elements, components, regions, layers, and/or sections should not be limited by these terms. These terms are only used to distinguish one limitation, element, component, region, layer, or section from another limitation, element, component, region, layer, or section. Thus, a first limitation, element, component, region, layer, or section discussed below could be termed a second limitation, element, component, region, layer, or section without departing from the teachings of the present application.

It will be further understood that when an element is referred to as being "on", "attached", "connected, or "coupled" to another element, it can be directly on or above, or connected or coupled to, the other element, or one or more intervening elements can be present. In contrast, when an element is referred to as being "directly on," 37 directly attached," "directly connected, or "directly coupled" to another element, there are no intervening elements present. Other words used to describe the relationship between elements should be interpreted in a like fashion (for example, "between" versus "directly between," "adjacent" versus "directly adjacent," etc.).

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations in addition to the orientation depicted in the figures. For example, if the figure is turned over, elements described as "below" and/or "beneath" other elements or features would then be oriented "above" the other elements or features.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

The present invention is direct to a universal dressing designed to fit snugly around various percutaneous tubes/drains/pins and tracheostomies. The outer layer dressing is designed to be impermeable to aid in the prevention of leakage of body secretions or fluids and to help prevent microbes from entering the body around the percutaneous device from the outside of the dressing.

Figure 1A:
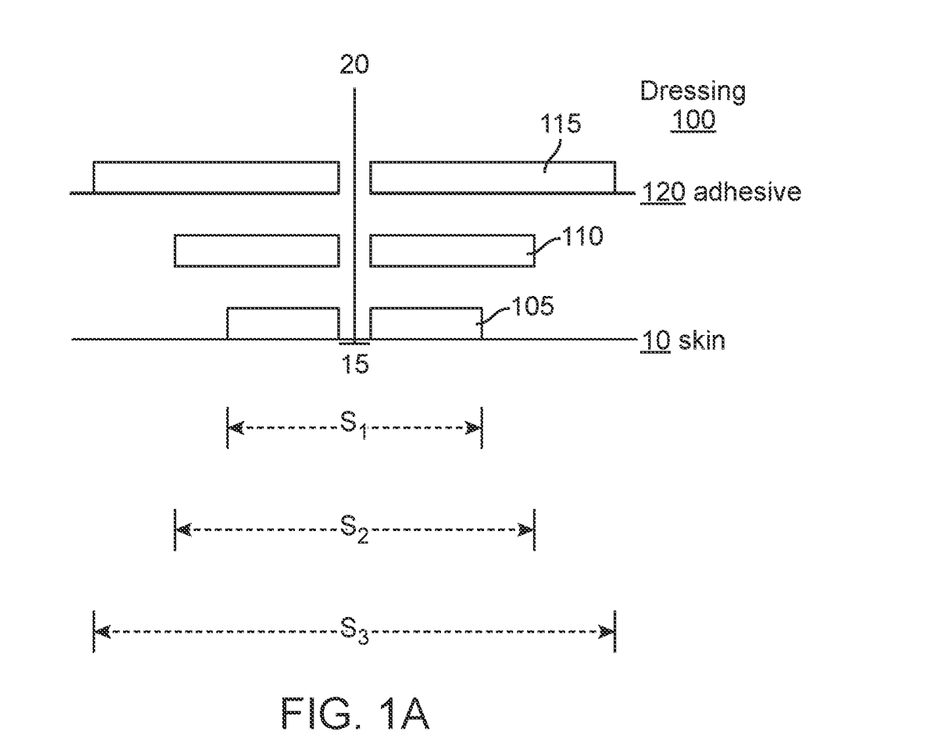
FIG. 1A shows an exploded cross-sectional view of a percutaneous tube dressing.
Figure 1B:
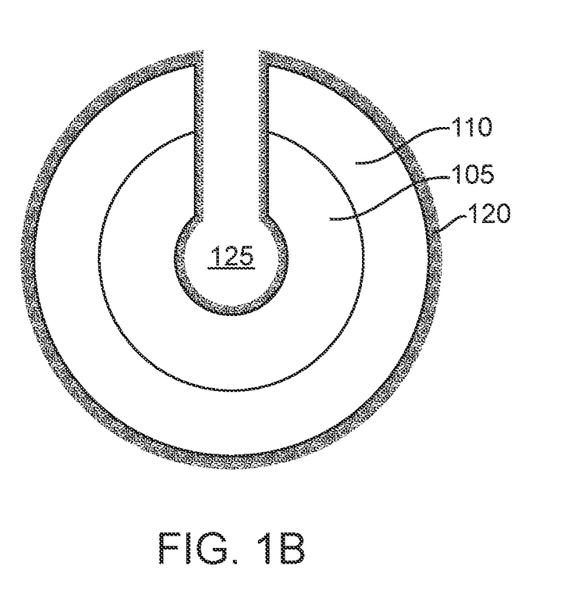
FIG. 1B shows a top view of the percutaneous tube dressing.
Figure 3:
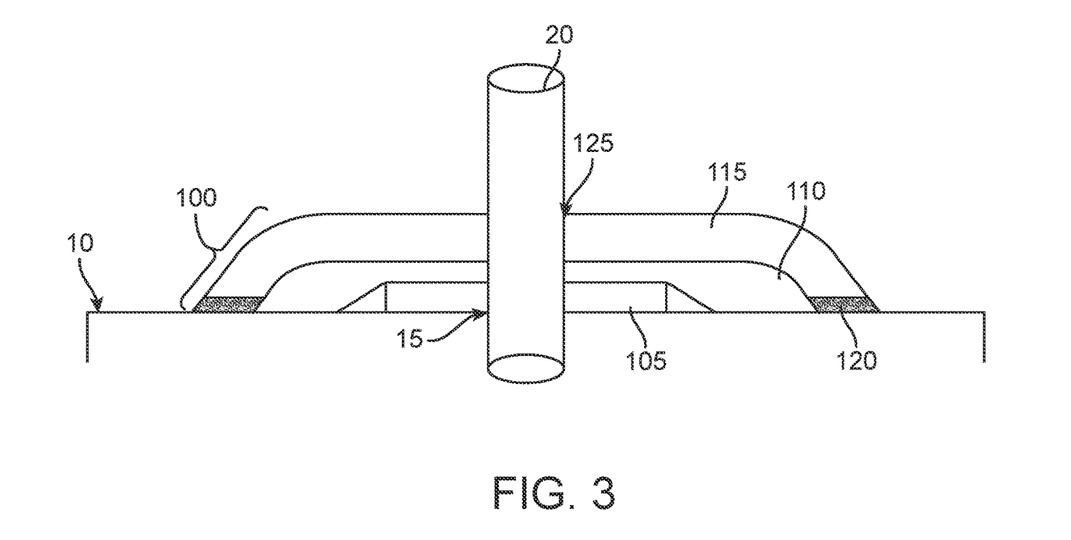
FIG. 3 shows the percutaneous tube dressing positioned on the skin proximate the closure site.

FIGS. 1A and 1B show an exploded cross-sectional view and a top view of a percutaneous tube dressing 100 that is designed to attach to the skin 10 and surround a percutaneous tube 20 and cover the tube closure site 15 (see FIG. 3). The dressing 100 is made with a unique combination of three or more layers including an antimicrobial, bactericidal and/or hemostatic or medicinal layer 105 positioned at the closure site 15, an absorbency layer 110, and a translucent or transparent impermeable layer 11S with an adhesive portion 120.

In some embodiments the unique percutaneous tube dressing 100 includes concentric overlapping layers 105, 110, 115 having different sizes or diameters, so that when stacked, each layer may or may not completely cover the layers below. For example, in the embodiment shown, therapeutic or antimicrobial layer 105 has a size of S1, absorbency layer 110 has a size of S2 and impermeable layer 115 has size S3. Layer 115 completely covers the other layers. The smaller layers are near the closure site and each subsequent layer is larger, S1<S2<S3. The skin adhesive portion 120 is distal to the perimeter of S3 so that it attaches directly to the skin 10. Layers 105, 110 below are embedded in the dressing forming a single unit. This allows the entire dressing 100 to be removed in its entirety 115 through 105, 110.

Figure 2:
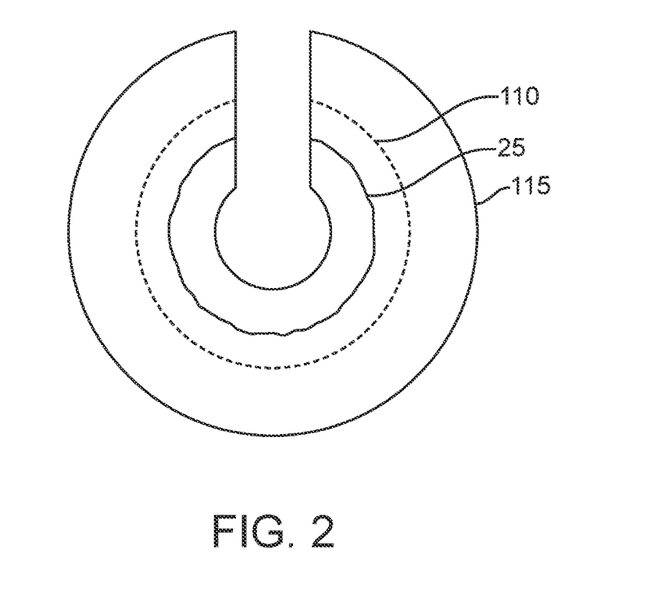
FIG. 2 shows the translucent or transparent impermeable layer viewing of fluids from the closure site soaked up by the absorbency layer.

FIG. 2 shows one embodiment of the translucent or transparent impermeable layer 115 allowing viewing of fluids 25 from the closure site 15 that has been soaked up by absorbency layer 110 without removal of the dressing 100. This allows viewing/assessment of the fluids around the surgical site/percutaneous drain site without having to completely remove the percutaneous tube dressing/surgical site dressing 100.

FIG. 3 shows the percutaneous tube dressing 100 positioned on the skin proximate the closure site 15 having a percutaneous tube 20 protruding from the skin closure site 15 after a medical procedure. The percutaneous tube dressing 100 includes the keyhole 125 sized to fit the percutaneous tube 20. Once the percutaneous tube 20 is positioned in the keyhole 125, the percutaneous tube dressing 100 is attached to the skin 10. Antimicrobial layer 105 is positioned over the closure site, the absorbency layer 110 is over or concentric with layer 105, outer layer 115 is positioned to cover both the antimicrobial layer 105 and absorbency layer 110. The adhesive portion 120 is then attached to the skin. In some embodiments, the adhesive portion 120 is distal the perimeter of layer 115 so that that adhesive portion 120 attaches to the skin and to the other layers 105, 110. This is a single dressing with the other components embedded in the single dressing 100.

In the embodiment shown, a percutaneous tube dressing 100 is designed to attach to the skin 10 and surround the percutaneous tube 20 and cover the closure site 15. The percutaneous tube dressing 100 is shown in an exaggerated schematic diagram as having a unique combination of three or more concentric or overlaying layers that may/can consist of antimicrobial, bactericidal and/or hemostatic or medicinal layers in any combination or location, such as 105, an absorbency layer 110 and outer translucent or transparent impermeable layer 115 with an adhesive portion 120. The translucent or transparent impermeable layer 115 allows viewing of the absorbency/or adjacent layer 110 to evaluate any fluids from the closure site 15.

The keyhole feature 125 is sized so the layers fit snugly around various size percutaneous tubes/drains/pins and tracheostomies 20 protruding from the skin 10 and cover the skin proximate the closure site 15. The layers 105, 110 and 115 are separate layers that are combined within the single dressing. (multiple layers; just showing three for simplicity).

The percutaneous tube dressing 100 may be any suitable shape, such as an oval shape, and may be designed to be ergonomic and fit the body to help prevent leakage of air or fluids when completely covering the intended area. The percutaneous tube dressing 100 may come in a range of sizes and shapes to fit multiple percutaneous devices and parts of the body. The percutaneous tube dressing 100 may seal the closure site sufficiently so that it can be used in the shower.

Layer 105 may be a single layer of material, or combination of layers, having antimicrobial, a bactericidal or hemostatic or medicinal agents that is located proximate the closure site. The closure site may be an operation closure site, or a site where a chest tube, tracheostomy tube, drain, or percutaneous pin exits the skin. Layer 105 may be made of antimicrobial, bactericidal, bacteriostatic, hemostatic, or medicinal components. In some embodiments, layer 105 may be made of Biopatch® disk (J&J) for infection or QuikClot® (Z-Medica) to promote blood clotting for examples.

Layer 110 may be a cushioned or absorbent layer positioned concentric or adjacent or overlying layer 105. The absorbent component is to allow fluid drainage, if present, from the site to be captured within the dressing while the cushioned component provides protection from pressure ulcers that can develop with percutaneous tubes resting directly on the skin. Layer 110 may be made of Mepilex® material (Convatec) for example.

Layer 115 is an outer cover layer made of an impermeable material designed to prevent fluid leakage from the dressing. Layer 115 is made of a material that is sufficiently transparent or translucent to allow viewing of any materials touching the transparent dressing. The transparency of the outer layer 115 can allow visualization of the fluids and/or the condition of the dressing which can aid in the indication of a need for dressing change. Layer 115 includes an adhesive portion configured to attach to the skin and the percutaneous device when wrapped around it to allow the dressing to remain in place. Layer 115 may be made of transparent material such as Opsite material (Smith and Nephew).

The keyhole feature 125 enables the dressing to be wrapped around the percutaneous device and the edges of the dressing can be crossed over one another to aid in securing the percutaneous device at the incision site allowing a tight seal to the device and skin. A film cover will be present on the underside of the dressing which will be removed to allow the dressing to be placed onto the skin (similar to the manner a band aid film is removed to expose the adhesive area). The dressing can be removed from the skin and device using standard methods.

Figure 4A:
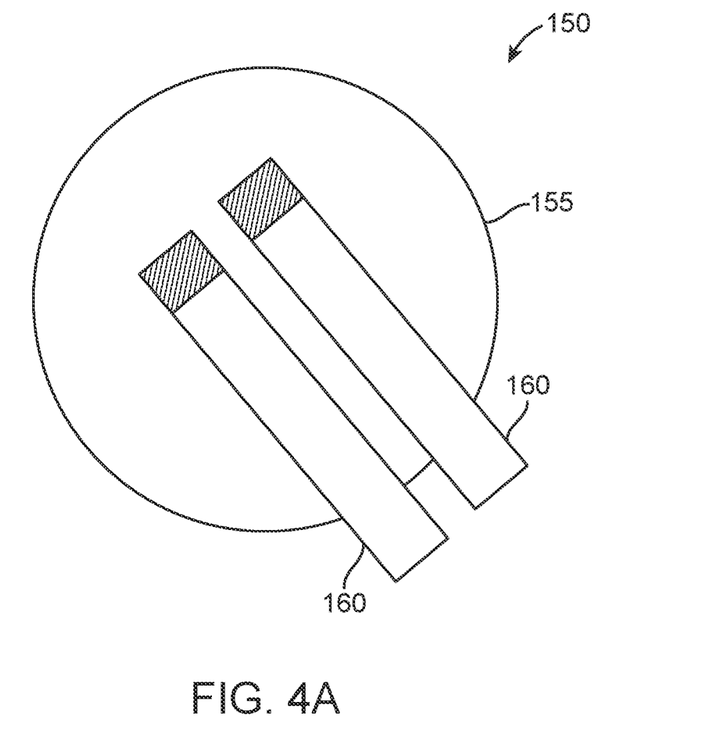
FIGS. 4A and 4B shows an additional dressing with adhesive strips on the top to help secure the tube to the body in a second location.
Figure 4B:
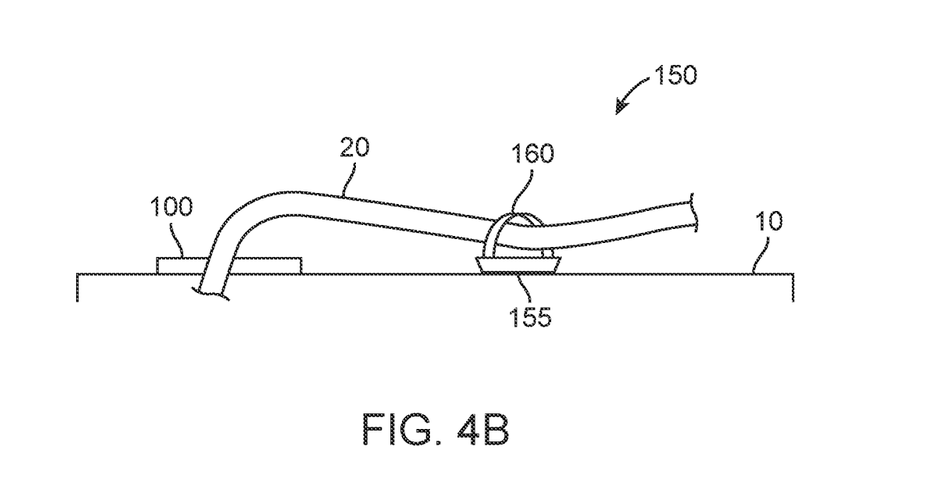
Figure 6:
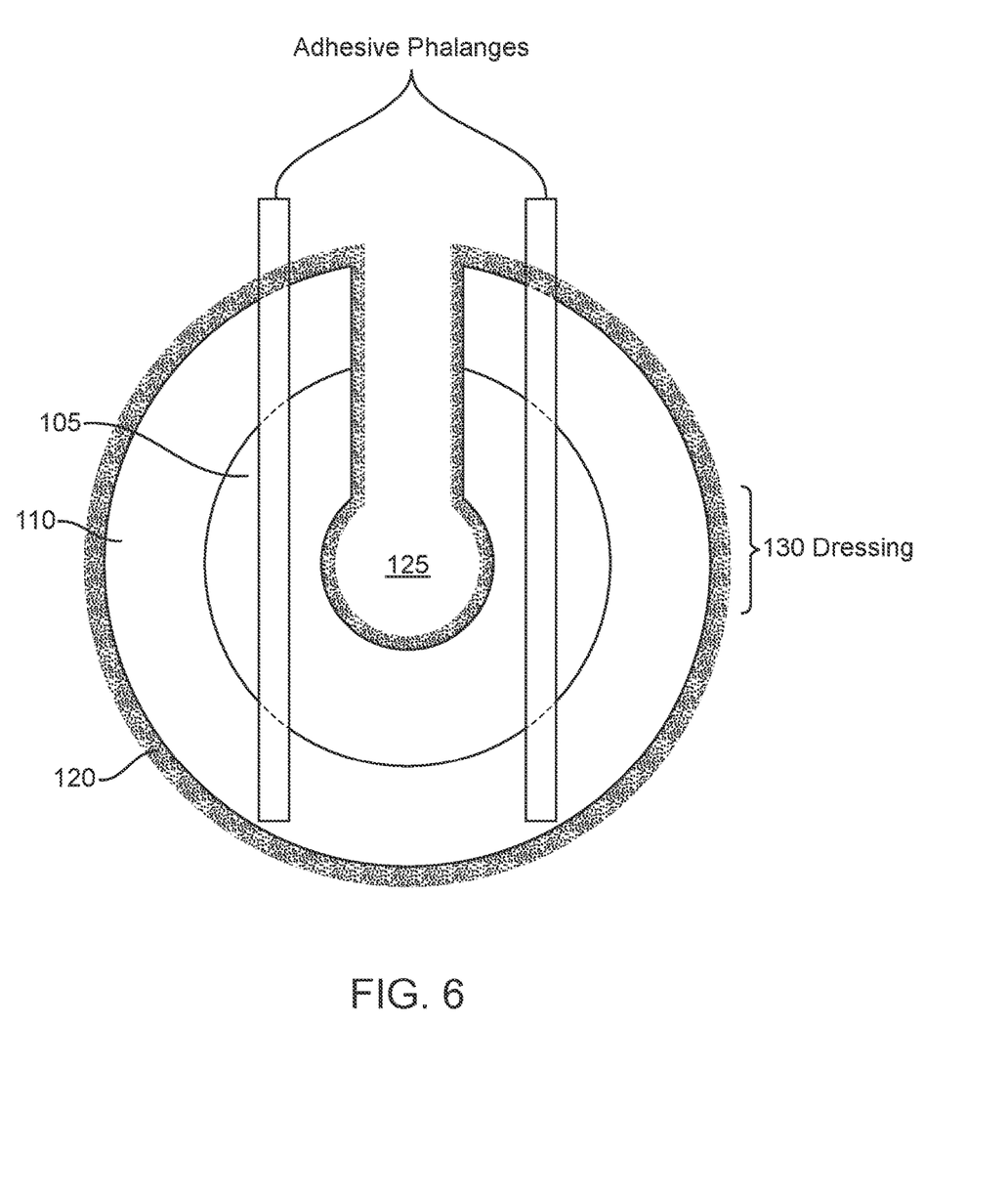
FIG. 6 shows another embodiment of a dressing.

A second embodiment 150, of the percutaneous device dressing 100 will be a dressing for additional securement of the percutaneous device. FIGS. 4A and 4B shows an additional dressing or second dressing for securement of the percutaneous device. The additional dressing is a shaped dressing 155 with a cushioned layer for better comfort and moisture absorption, and one or more adhesive strips 160 on the top 115 of the dressing to help secure the device to the body by securing the device to the dressing. Some percutaneous devices may require this additional dressing in a second location or this dressing alone dressing 130 with adhesive strips (dressing 100 with adhesive strips), see FIG. 6. This embodiment aids in the prevention of accidental removal of the percutaneous tube with movement. The additional dressing is designed to secure the percutaneous tube/device in place to the body and the adhesive strips on the top of the cushioned dressing 150 or dressing 130 will keep the percutaneous tube secure. It will aid in the prevention of the percutaneous tube dislodging. In some embodiments, the adhesive strips can be placed one proximal and one distal to the connection, for example, when used with a chest tube connection to the atrium or other connecting device.

Figure 5:
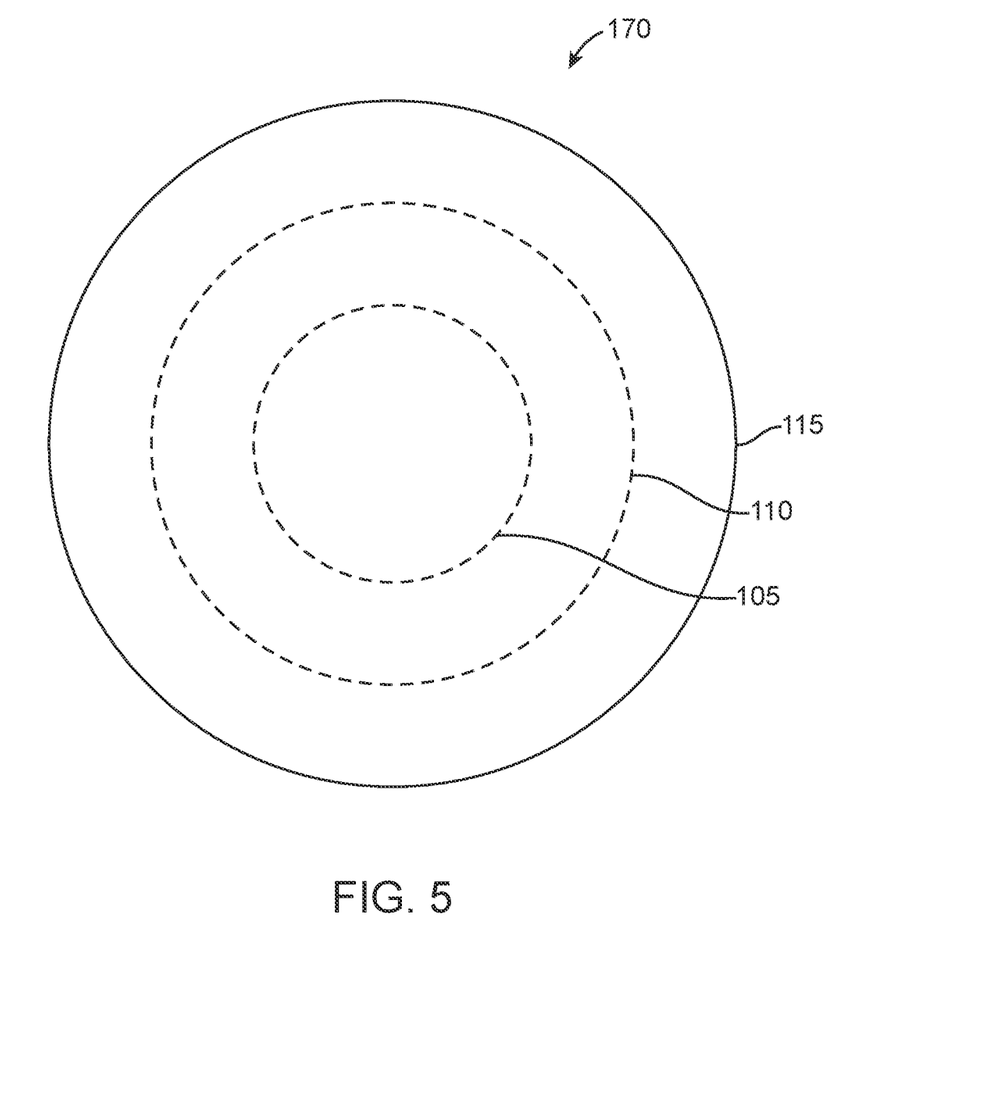
FIG. 5 is a top view of a closure site dressing.

FIG. 5 is a top view of the third embodiment of dressing 100 where the additional dressing, is a closure site dressing 170 that will be used once the device 20 has been removed from the body. The dressing 170 is placed on the opening where the percutaneous device was removed to cover the site. The closure site dressing 170 will consist of the layers described above, the antimicrobial, bactericidal and/or hemostatic or medicinal layer 105, the absorbency layer 110, and the translucent or transparent impermeable layer 115 with an adhesive portion 120. However, the closure site dressing 170 will not have a keyhole. It can vary in shape and have a see-through adhesive layer 115. The layers 105, 110, 115 will include different sizes or diameters, as described in paragraph 0025 without the keyhole. Transparent impermeable layer 115 is made of an impermeable material designed to prevent fluid leakage from the dressing and is sufficiently transparent or translucent to allow viewing of any materials touching the transparent layer.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A unitary percutaneous tube, positive pressure dressing with components including multiple concentric overlapping layers, the dressing comprising:
    a first component having an inner treatment layer configured to cover a percutaneous tube closure site on a patient, the side of the treatment layer to be engaged with the skin of the patient non-adhesively, being coated with therapeutic agents;
    a second component having an absorbent layer sized to cover and completely surround the inner treatment layer; and
    a third component having an impermeable layer having an outer perimeter, the impermeable layer being sized to cover and completely surround the absorbent layer and inner treatment layer, the impermeable layer having a peripheral adhesive portion radially distal to the outer perimeter of the impermeable layer and configured to attach to the patient's skin surrounding the absorbent layer and the inner treatment layer, the impermeable layer being transparent or translucent to allow viewing of the absorbent layer and fluids from the closure site which have been absorbed up by the absorbent layer and further having phalanges integrally formed as part of the impermeable layer to secure the dressing to a percutaneous tube that resides within the percutaneous tube closure site;
    wherein the inner treatment layer, absorbent layer, and impermeable layer are generally concentric overlapping layers having increasing sizes or diameters, so that the impermeable layer covers and overlaps the absorbent layer, which absorbent covers and overlaps the inner treatment layer and each layer is formed as an integral part of the dressing to form a single unit multi-layered dressing with integral phalanges.

2. The unitary percutaneous tube dressing of claim 1, wherein the inner treatment layer is a single layer of being coated with therapeutic material selected from antimicrobial, bactericidal, or hemostatic, or medicinal agents selectively including an analgesic, CBD, or marijuana derived substance.

3. The unitary percutaneous tube dressing of claim 1, wherein the inner treatment layer is a combination of layers having antimicrobial, bactericidal or hemostatic, or medicinal agents selectively including include an analgesic, CBD, or marijuana derived substance.

4. The unitary percutaneous tube dressing of claim 1, wherein the impermeable layer is configured to prevent leakage of body secretions or fluids from the percutaneous tube dressing.

5. The unitary percutaneous tube dressing of claim 1, wherein the impermeable layer is configured to help prevent microbes from entering the body around the percutaneous device from the outside of the percutaneous tube dressing.

6. The unitary percutaneous tube dressing of claim 1, wherein the inner treatment layer, absorbent layer, and impermeable layer include a keyhole sized to fit the percutaneous tube, thereby allowing the unitary percutaneous tube dressing to lie flat on the skin surrounding the percutaneous tube.

7. The unitary percutaneous tube dressing of claim 1, further comprising a second dressing having a cushioned layer configured to attach to the patient's skin at a second location, the second dressing having at least one adhesive strip configured to couple with the percutaneous tube to prevent the percutaneous tube from dislodging.

8. A unitary percutaneous tube, positive pressure dressing with multiple concentric overlapping layers comprising:
an inner layer having therapeutic treatment material and sized to cover a percutaneous tube closure site, the side of the inner layer to be engaged with the skin of the patient being non-adhesive and therapeutic;
an intermediate layer of absorbent material sized to cover and completely surround the inner layer; and
an outer layer of impermeable material covering and completely surrounding the inner layer, the intermediate layer having an adhesive portion configured to attach to the patient's skin surrounding the percutaneous tube closure site and further having phalanges integrally formed as part of the impermeable layer to secure the dressing to a percutaneous tube that resides within the percutaneous tube closure site;
wherein the inner layer, intermediate layer, and outer layer are generally concentric overlapping layers having increasing sizes or diameters, so that when stacked, each layer completely covers the layer below and each layer is formed as an integral part of the dressing to form a single unit multi-layered dressing with integral phalanges.

9. The unitary percutaneous tube dressing of claim 8, wherein the inner layer is a single layer of the treatment material being coated with therapeutic material selected from antimicrobial, bactericidal, or hemostatic, or medicinal agents and selectively including an analgesic, CBD, or marijuana derived substance.

10. The unitary percutaneous tube dressing of claim 8, wherein the inner layer is a combination of layers of the therapeutic treatment material having antimicrobial, bactericidal, or hemostatic, or medicinal agents selectively including include an analgesic, CBD, or marijuana derived substance.

11. The unitary percutaneous tube dressing of claim 8, wherein the impermeable material is configured to prevent leakage of body secretions or fluids from the percutaneous tube dressing.

12. The unitary percutaneous tube dressing of claim 8, wherein the impermeable material that is a translucent or transparent material configured to allow the fluids and/or the condition of the intermediate layer to be viewed, which aids in the indication of a need to replace the unitary percutaneous tube dressing.

13. The unitary percutaneous tube dressing of claim 8, wherein the inner layer, the intermediate layer, and the outer layer include a keyhole sized to fit the percutaneous tube.

14. The unitary percutaneous tube dressing of claim 8, further comprising a second dressing having a cushioned layer configured to attach to the patient's skin at a second location, the second dressing having at least one adhesive strip configured to couple with the percutaneous tube to prevent the percutaneous tube from dislodging.

15. A unitary percutaneous tube, positive pressure dressing with multiple concentric overlapping layers comprising:
an inner layer including a therapeutic treatment material configured to non-adhesively cover a patient's percutaneous tube closure site at a first location;
an intermediate layer including an absorbent material sized to completely surround the inner layer; and
outer layer including an impermeable material sized to completely surround the intermediate layer, the outer layer having an adhesive portion configured to attach to the patient's skin surrounding the percutaneous tube closure site and further having phalanges integrally formed as part of the impermeable layer to secure the dressing to a percutaneous tube that resides within the percutaneous tube closure site;
wherein, the inner layer, the intermediate layer, and the outer layer include a keyhole sized to fit the percutaneous tube;
wherein the inner layer, intermediate layer, and outer layer are generally concentric overlapping layers having increasing sizes or diameters, so that when stacked, each layer completely covers the layer below and each layer is formed as an integral part of the dressing to form a single unit multi-layered dressing with integral phalanges; and
a second dressing having a cushioned layer configured to attach to the patient's skin at a second location spaced from the first location, the second dressing having at least one adhesive strip configured to couple with the percutaneous tube to prevent the percutaneous tube from dislodging.

16. The unitary percutaneous tube dressing of claim 15, wherein the unitary percutaneous tube dressing is oval in shape.

17. The unitary percutaneous tube dressing of claim 15, wherein the therapeutic treatment material is selected from the group consisting of: CBC infused; Marijuana component; Zinc; and a silver sulfonamide antibiotic.

18. The unitary percutaneous tube dressing of claim 15, wherein the absorbent material is selected from the group consisting of: a hydrocolloid; and an anti-microbial foam.

19. The unitary percutaneous tube dressing of claim 15, wherein the cushioned layer is a cushioning material selected from the group consisting of: a breathable hydrocolloid biodegradable wound adherent; non-adherent cotton pads; a carboxymethyl cellulose fiber; an occlusive fine mesh gauze; an Antimicrobial; and Silicone.

20. The unitary percutaneous tube dressing of claim 1, wherein the unitary percutaneous tube dressing is oval in shape.

21. The unitary percutaneous tube dressing of claim 1, and further comprising at least one adhesive strip secured to the upper surface of the impermeable layer and configured to be secured to the percutaneous tube.

22. The unitary percutaneous tube dressing of claim 8, wherein the unitary percutaneous tube dressing is oval in shape.

23. The unitary percutaneous tube dressing of claim 8, and further comprising at least one adhesive strip secured to the upper surface of the impermeable layer and configured to be secured to the percutaneous tube.

24. The unitary percutaneous tube dressing of claim 15, and further comprising at least one adhesive strip secured to the upper surface of the impermeable layer and configured to be secured to the percutaneous tube.

25. The unitary percutaneous tube dressing of claim 8, wherein the impermeable material that is a translucent or transparent material configured to allow the fluids and/or the condition of the intermediate layer to be viewed, which aids in the indication of a need to replace the unitary percutaneous tube dressing.

* * * * *